United States Patent [19]

Butler et al.

[11] Patent Number: 4,916,202

[45] Date of Patent: Apr. 10, 1990

[54] EPOXY RESIN

[75] Inventors: John M. Butler, Centerville; Richard P. Chartoff, Cincinnati; James A. Harvey, Kettering, all of Ohio

[73] Assignee: University of Dayton, Dayton, Ohio

[21] Appl. No.: 98,091

[22] Filed: Sep. 17, 1987

[51] Int. Cl.$^4$ .................... C08G 59/24; C08G 59/28; C08G 59/30

[52] U.S. Cl. ........................ 528/98; 528/99; 549/522

[58] Field of Search ................. 528/98, 99; 549/552

[56] References Cited

U.S. PATENT DOCUMENTS

| | | | |
|---|---|---|---|
| 2,951,822 | 9/1960 | Reinking | 528/103 |
| 3,014,895 | 12/1961 | Reynolds et al. | 528/391 |
| 3,312,664 | 4/1967 | Boemmer | 528/99 |
| 3,843,565 | 10/1974 | Yamamoto et al. | 525/482 |
| 3,945,973 | 3/1976 | Smith et al. | 528/210 |
| 4,107,128 | 8/1978 | Hosoi et al. | 523/434 |
| 4,161,588 | 7/1979 | Green et al. | 549/218 |
| 4,269,759 | 5/1981 | Edelman | 523/468 |
| 4,487,948 | 12/1984 | Shimp et al. | 549/552 |
| 4,518,786 | 5/1985 | Wang et al. | 549/552 |
| 4,540,769 | 9/1985 | Dobinson et al. | 528/90 |
| 4,560,739 | 10/1985 | Zahir | 528/99 |
| 4,594,373 | 6/1986 | Kohli | 523/400 |
| 4,607,069 | 8/1986 | Tesch et al. | 523/400 |
| 4,636,535 | 1/1987 | Wang et al. | 523/204 |
| 4,645,803 | 3/1987 | Kohli et al. | 525/423 |
| 4,665,150 | 5/1987 | Tesch et al. | 528/98 |
| 4,680,341 | 7/1987 | Newman-Evans | 525/113 |

FOREIGN PATENT DOCUMENTS 62-00477  1/1987  Japan.
62-146917  6/1987  Japan.

OTHER PUBLICATIONS

Morimoto et al., "Epoxy Resin", Chemical Abstracts, 107, 155397m (1987).

Suzue et al., "Epoxy Resin Compositions for Prepregs", Chemical Abstracts, 108, 39024j (1988).

"Swelling and Glass Transition Relations for Epoxy Matrix Material in Humid Environments", McKague et al., Journal of Applied Polymer Science, vol. 22, 1643–1654, 1978.

"Interaction of Epoxy Resins with Water: The Depression of Glass Transition Temperature," Ellis et al., Polymer, vol. 25, May 1984.

Primary Examiner—Earl Nielsen
Attorney, Agent, or Firm—Biebel, French & Nauman

[57] ABSTRACT

The present invention provides an epoxy resin of the formula

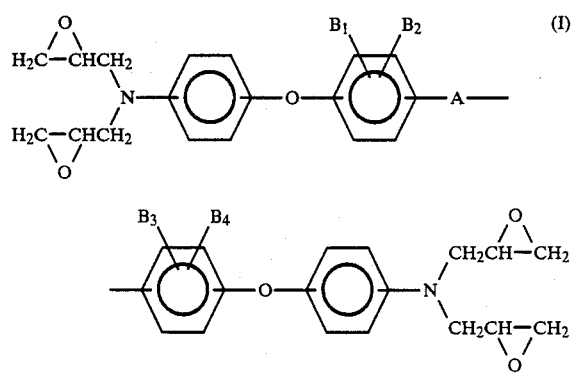

where A is selected from the group consisting of $-C(CH_3)_2-$, $-C(CF_3)_2-$, $-S-$, $-SO_2-$, $-CH_2-$, $-CO-$, $-O-$, and $-C_3H_6-$, and each $B_1$, $B_2$, $B_3$, and $B_4$ is independently selected from the group consisting of $-H$, $-F$, $-Cl$, $-Br$, $-I$, $-CH_2CH=CH_2$, $-CH_3$, $-C_2H_5$, $-C_3H_7$, and $-C_4H_9$.

The present invention also provides a curable composition comprising an epoxy resin of the foregoing formula (I) and an effective curing amount of a hardener for an epoxy resin. The moisture sensitivity of the cured castings and/or composites based on the epoxy resins is lower than known epoxy resin castings and/or composites that have comparable thermal stability, modulus, strength, processability, and toughness.

4 Claims, No Drawings

EPOXY RESIN

BACKGROUND OF THE INVENTION

The present invention relates to epoxy resins.

Currently, epoxy resins are being used in composites in various industrial applications. For example, epoxy composites are used as circuit boards for the electronic industry and as structural members for aeronautical purposes. A critical problem in the use of epoxy resins for structural components is the extensive loss in thermal and mechanical properties (heat distortion point, strength, and modulus) when exposed to hot/wet conditions. A variety of approaches have been reported in attempts to overcome this shortcoming. Many have given a reduction in water absorption, and thus, less loss in properties in hot/wet conditions but in so doing they have compromised some of the other desirable properties such as thermal and/or oxidative stability, heat distortion temperature, toughness, and ease of formulations.

Epoxy resins made from aliphatic amines are disclosed in U.S. Pat. No. 3,843,565. Epoxy resins made from sulfonamides are disclosed in U.S. Pat. No. 3,945,973. Epoxy resins made from aromatic amines are disclosed in U.S. Pat. Nos. 2,951,822; 3,014,895; 3,312,664; 4,107,128; 4,161,588; 4,269,759; 4,487,948; 4,518,786; 4,540,769; and 4,560,739. U.S. Pat. No. 4,540,769 teaches epoxy resins made from aromatic amines such as bis(4-aminophenyl)ether.

One commercial epoxy resin is tetraglycidyl-4,4'-(4-aminophenyl)-p-diisopropylbenzene which has the following structure as disclosed in U.S. Pat. No. 4,680,341:

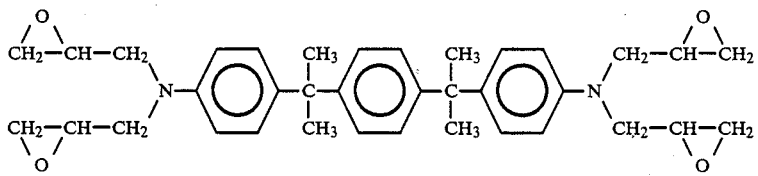

This resin is commercially available from the Shell Chemical Company as EPON HPT 1071.

Another commercial epoxy resin is tetraglycidyl-4,4'-(3,5-dimethyl-4-aminophenyl)-p-diisopropylbenzene which has the following structure:

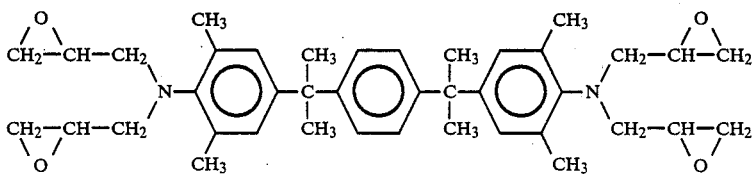

This resin is commercially available from the Shell Chemical Company as EPON HPT 1072.

A widely used epoxy resin in the aeronautical industry is tetraglycidyl 4,4'-diamino diphenyl methane which has the formula:

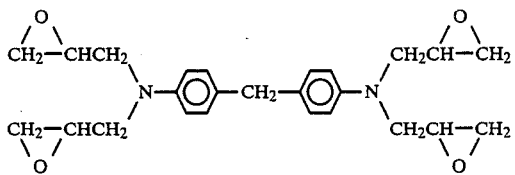

This epoxy resin is commercially available from Ciba-Geigy Corporation as ARALDITE (registered trademark) MY-720. As the resin is prepared by reacting epichlorohydrin with methylene dianiline, it is frequently identified as tetraglycidylated methylene dianiline (hereinafter TGMDA).

While each epoxy esin discussed above has a number of desirable properties, each is deficient in one or more properties desired in the art. For example, the cured TGMDA resins are extremely moisture sensitive, and hence, subject to degradation of properties at high humidities. The impact strength and toughness of these resins are lower than those obtainable with other resins systems.

Many of the cured epoxy resins discussed above absorb substantial quantities of moisture from the atmosphere. A high moisture content significantly lowers the glass transition temperature (Tg) of the cured resins as compared with the values obtained with the bone dry resins. As a result, the decrease of the glass transition temperature decreases the effective maximum temperature at which the cured epoxy resins and composites prepared therefrom can be employed. The shortcomings of the state-of-the-art epoxy resins are discussed in the following references: Apicella et al, *I and E Chem.: Prod. Dev.*, 288 (1984); Browning, *Polymer Eng. Sci.*, 18, 16 (1978); McKague, *J. Appl. Polymer Sci.*, 22, 1643 (1978); Ellis et al, Polymer 25(2), 664 (1984); and Bauer, *31st International SAMPE Symposium* (1986).

SUMMARY OF THE INVENTION

The present invention provides an epoxy resin of the formula (I)

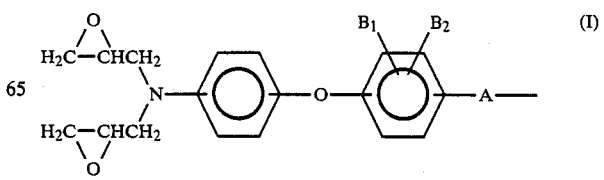

-continued

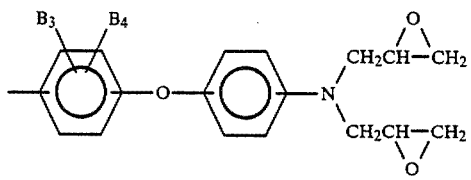

where A is selected from the group consisting of —C(CH$_3$)$_2$—, —C(CF$_3$)$_2$—, —S—, —SO$_2$—, —CH$_2$—, —CO—, —O—, and —C$_3$H$_6$—, and each B$_1$, B$_2$, B$_3$, and B$_4$ is independently selected from the group consisting of —H, —F, —Cl, —Br, —I, —CH$_2$CH=CH$_2$, —CH$_3$, —C$_2$H$_5$, —C$_3$H$_7$, and —C$_4$H$_9$.

These resins can be cured with known epoxy resin hardeners to provide cured resins having superior performance properties including excellent moisture resistance and thermal stability as compared with presently available commercial epoxy resins.

In a preferred embodiment, A is —C(CH$_3$)$_2$— and B$_1$, B$_2$, B$_3$, and B$_4$ are —H. This epoxy resin is bisphenol A ether diamine epoxy (hereinafter BPAE). This embodiment is preferred because cured systems based thereon have low moisture sensitivity.

In another embodiment, A is —C(CF$_3$)$_2$— and B$_1$, B$_2$, B$_3$, and B$_4$ are —H. This embodiment is preferred because it has a low dielectric constant.

Thus, an object of the present invention is to provide epoxy resins which can be cured to a polymer network which is less moisture sensitive than conventional composites and/or castings while maintaining high thermal stability and excellent mechanical properties.

A further object of the present invention is to provide epoxy resins which are useful as matrix resins for structural composites, for circuit boards for the electronic industry, as structural adhesives, and as surface coatings.

Other objects and advantages of the present invention will be apparent from the following description and the appended claims.

DETAILED DESCRIPTION OF THE INVENTION

As noted supra, the epoxy resins of the present invention conform to the formula (I):

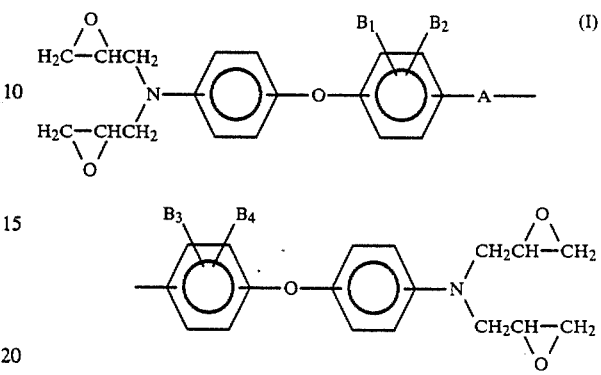

The structure of the epoxy resins of formula (I) can be varied in several respects. As a consequent, cured resin systems having modified properties are readily prepared.

Each of the diglycidylamino groups can be attached to the terminal phenyl group at a position ortho, meta, or para with respect to the ether oxygen atom. Each set of diglycidylamino groups can be attached at the same or different positions with respect to the ether oxygen atoms. The packing or tightness of the cured cross-linked polymer network can be affected by such selections to provide resins having enhanced or reduced flexibility as desired.

In a preferred embodiment, A is —C(CF$_3$)— and B$_1$, B$_2$, B$_3$, and B$_4$ are —H. This compound has the formula (II):

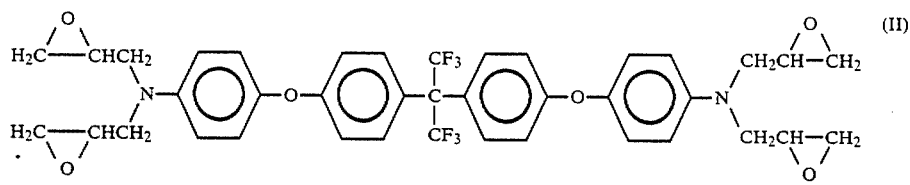

In another preferred embodiment, A is —C(CH$_3$)$_2$— and B$_1$, B$_2$, B$_3$, and B$_4$ are —H. This compound has the formula (III):

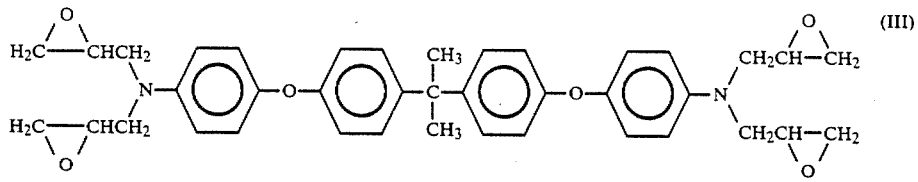

The epoxy resins of formula (I) are readily prepared by synthesis methods known in the art. Specifically, an appropriate bis(aminoaryl)diether of formula (IV) can be reacted with epihalohydrin, preferably, epichlorohydrin, in the presence of sodium hydroxide as shown below:

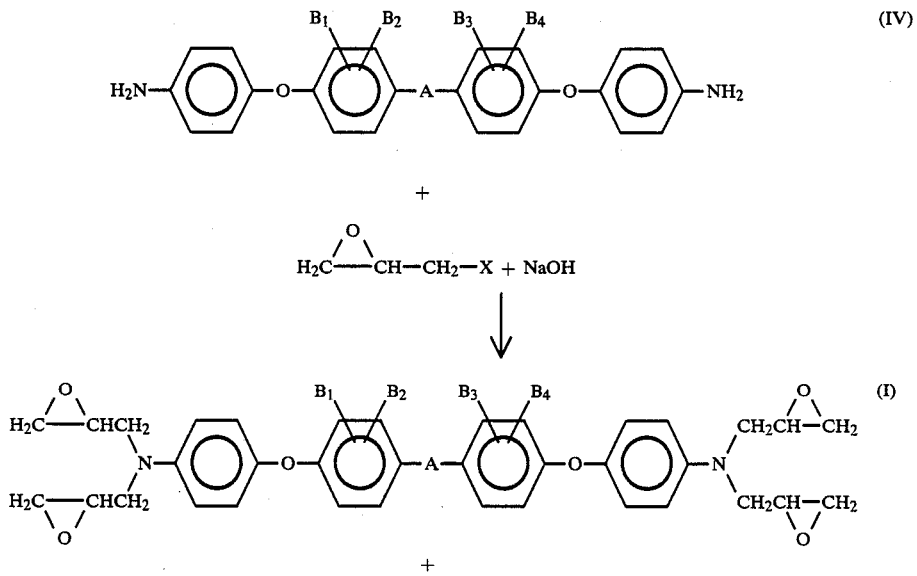

The bis(aminoaryl) diethers of formula (IV) can be prepared by reacting a bisphenol, e.g., bisphenol A, with two mols of a chloronitrobenzene in the presence of an inorganic base to prepare a bis(nitrophenyl)-diether of formula (V). The bis(nitrophenyl)diether of formula (V) is then reduced to provide the bis(aminophenyl)diether of formula (IV). This reduction can be effected with hydrazine hydrate in the presence of a palladium catalyst supported on charcoal or by other suitable methods. The overall synthesis steps are shown below:

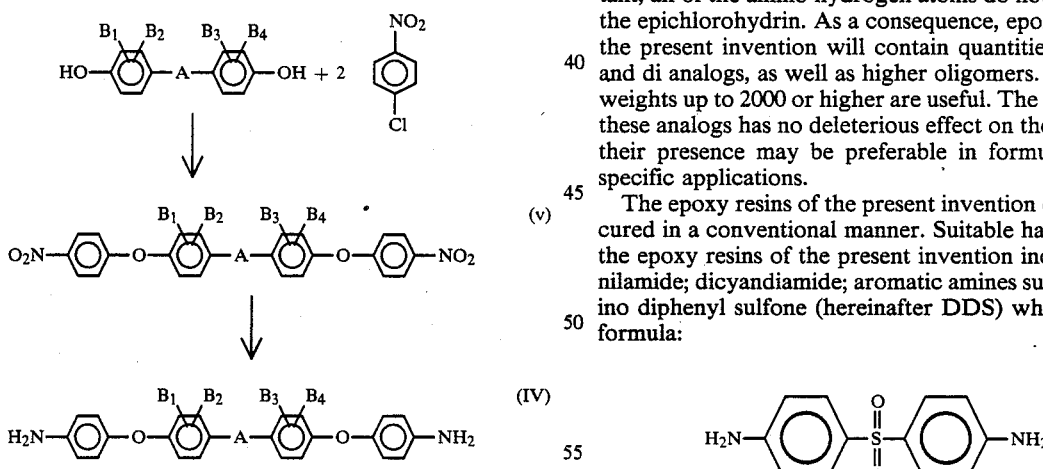

Diamines can also be prepared according to the methods of the following references: J. A. Harvey, R. P. Chartoff, and J. M. Butler, 18th *International SAMPE Technical Conference Proceedings*, 705 (1986) (2,2-bis[4-(4-aminophenoxy)phenyl]propane and others); Brode et al, *Polymer Reprints* 15(*i*), 761 (1974) (bis[4-(4-aminophenoxy)phenyl]sulfone); and U.S. Pat. No. 4,203,922 (2,2-bis[4-(4-aminophenoxy)phenyl]-1,3-trifluoropropane).

Suitable epihalohydrins which can be employed in the present invention include epichlorohydrin, epibromohydrin, epiiodohydrin, and mixtures thereof.

Based on the stoichiometry of the reaction, at least 4 moles of epichlorohydrin are needed to react with 1 mole of diamine or 1 equivalent of epichlorohydrin per amino hydrogen equivalent of the diamine. Typically, about 0.5 to 8.0 equivalents of epichlorohydrin are used per amino hydrogen equivalent of the diamine.

By reason of steric and other possible factors, the experimentally determined epoxy equivalent weights of the epoxy resins of the present invention are somewhat higher than the theoretical. This results because with a small percentage of bis(aminoaryl)diaryldiether reactant, all of the amino hydrogen atoms do not react with the epichlorohydrin. As a consequence, epoxy resins of the present invention will contain quantities of the tri and di analogs, as well as higher oligomers. Equivalent weights up to 2000 or higher are useful. The presence of these analogs has no deleterious effect on the resins and their presence may be preferable in formulations for specific applications.

The epoxy resins of the present invention can then be cured in a conventional manner. Suitable hardeners for the epoxy resins of the present invention include sulfanilamide; dicyandiamide; aromatic amines such as diamino diphenyl sulfone (hereinafter DDS) which has the formula:

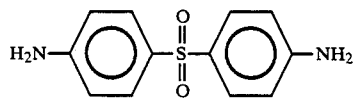

bis(4-aminophenyl) methane; the bis(aminophenyl)-diethers of formula (IV) including 2,2-bis [4-[4-aminiophenoxy) phenyl]-1,3-trifluoropropane; bis[4-(4-aminophenoxy) phenyl]sulfone; and bisphenol A ether diamine (hereinafter BPADA) which as the formula:

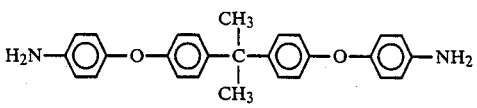

m-phenylenediamine; p-phenylenediamine; 1,6-diaminonaphthalene; 4,4'-diaminodiphenyl ether; 3-methyl-4-aminobenzamide; alpha, alpha'-bis(4-aminophenyl)-metadiisopropylbenzene; alpha, alpha'-bis(4-aminophenyl)-para-diisopropylbenzene; 1,3-bis(4-aminophenyl)benzene; and 1,3-bis(3-aminophenoxy) benzene; and polycarboxylic acid anhydrides such as hexahydrophthalic acid dianhydride; methylbicyclo[2,2,1]-hept-5-ene-2,3-dicarboxylic acid anhydride; pyromellitic acid dianhydride; bis-2,2-(4-phthalicanhydrido)hexafluoropropane; and benzophenone tetracarboxylic acid dianhydride. The preferred hardeners are DDS and BPADA.

The amount of hardener employed to cure the epoxy resins of the present invention will approximate the quantities employed with the presently used commercial resins such as MY-720, EPON HPT 1071, EPON HPT 1072, and EPON 828. Typically, up to 1.5 equivalent weight of hardener is used per one equivalent weight of the epoxy resin; preferably, about 0.5 to 1.0 equivalent weight of hardener is used per one equivalent weight of epoxy resin. Depending upon the nature of the hardener, curing can be performed at room temperature or at elevated temperatures. Curing provides a crosslinked polymer network which is infusible and intractable.

The epoxy resin system may additionally contain an accelerator to increase the rate of cure. Accelerators which may be used herein include Lewis acid/amine complexes such as $BF_3$/monoethylamine, $BF_3$/piperidiene, $BF_3$/methylimidazole; amines, such as imidazole and its derivatives such as 4-ethyl-2-methylimidazole, 1-methylimidazole, 2-methylimidazole; N,N-dimethylbenzylamine; acid salts of tertiary amines, such as the p-toluenesulfonic acid/imidazole complex, salts of trifluoromethane sulfonic acid, such as FC-520 (obtained from 3M Company), organophosphonium halides, dicyandiamide, 1,1-dimethyl-3-phenyl urea (Fikure (62U from Fike Chemical Co.) and chlorinated derivatives of 1,1-dimethyl-3-phenyl urea (monuron and diuron from du Pont). If used, the amount of cure accelerator may be from 0.02 to 10 percent of the weight of the epoxy resin system (i.e., epoxy plus hardener).

The epoxy resins of the present invention can also be mixed with conventional epoxy resins prior to curing. The conventional epoxy resins used may be present in an amount up to about 40 wt.%, preferably up to about 30 wt% based on the amount of the epoxy resin of the present invention used.

The conventional epoxy resins which may be used herein contain two or more epoxy groups. The epoxy groups can be terminal epoxy groups or internal epoxy groups. The epoxides are of two general types: polyglycidyl compounds or products derived from epoxidation of dienes or polyenes. Polyglycidyl compounds contain a plurality of 1,2-epoxide groups derived from the reaction of a polyfunctional active hydrogen containing compound with an excess of an epihalohydrin under basic conditions. When the active hydrogen compound is a polyhydric alcohol or phenol, the resulting epoxide composition contains glycidyl ether groups.

Polyepoxides which are polyglycidyl ethers of 4,4'-dihydroxyphenyl methane, 4,4'-dihydroxyphenyl sulfone, 4,4'-dihydroxydiphenyl sulfide, phenolphthalein, resorcinol, or tris(4-hydroxyphenyl)methane and the like are useful in this invention. In addition, EPON 1031 (a tetraglycidyl derivative of 1,1,2,2-tetrakis(hydroxyphenyl) ethane from Shell Chemical Company), and Apogen 101, (a methylolated bisphenol A resin from Schaefer Chemical Co.) may also be used. Halogenated polyglycidyl compounds such as D.E.R. 542 (a brominated bisphenol A epoxy resin from Dow Chemical Company) are also useful. Other suitable epoxy resins include polyepoxides prepared from polyols such as pentaerythritol, glycerol, butanediol, or trimethylolpropane and an epihalohydrin.

Other polyfunctional active hydrogen compounds besides phenols and alcohols may be used to prepare the polyglycidyl adducts useful in this invention. They include amines, aminoalcohols, and polycarboxylic acids.

Suitable polyglycidyl adducts derived from aminoalcohols include O,N,N-triglycidyl-4-aminophenol available as Araldite 0500 or Araldite 0510 (obtained from Ciba-Geigy Corporation) and O,N,N-triglycidyl-3-aminophenol (available as Glyamine 115 from F.M.C. Corporation).

Also suitable for use herein are the glycidyl esters of carboxylic acids. Such glycidyl esters include, for example, diglycidyl phthalate, diglycidyl terephthalate, diglycidyl isophthalate, and diglycidyl adipate. There may also be used polyepoxide such as triglycidyl cyanurates and isocyanurates, N,N-diglycidyl oxamides, N,N'-diglycidyl derivates of hydantoins such as "XB 2793" (obtained from Ciba-Geigy Corporation), diglycidyl esters of cycloaliphatic dicarboxylic acids, and polyglycidyl thioethers of polythiols.

Other epoxy-containing materials are copolymers of acrylic acid esters of glycidol such as glycidyl acrylate and glycidyl methacrylate with one or more copolymerizable vinyl compounds. Examples of such copolymers are 1:1 styrene-glycidyl methacrylate, 1:1 methyl methacrylate-glycidyl acrylate and 62.5:24:13.5 methyl methacrylate:ethyl acrylate:glycidyl methacrylate.

Silicone resins containing epoxy functionality, e.g., 2,4,6,8,10-pentakis[3-(2,3-epoxypropoxy)propyl]-2,4,6,8,10-pentamethylcyclopentasiloxane and the diglycidyl ether of 1,3-bis-(3-hydroxypropyl)tetramethyldisiloxane are also useable.

The second group of conventional epoxy resins is prepared by epoxidation of dienes or polyenes. Resins of this type include bis(2,3-epoxycyclopentyl)ether copolymers with ethylene glycol which are described in U.S. Pat. No. 3,398,102, 5(6)-glycidyl-2-(1,2-epoxyethyl) bicyclo[2.2.1]heptane and dicyclopentadiene diepoxide. Commercial examples of these epoxides include 3,4-epoxy-6-methylcyclohexylmethyl 3,4-epoxy-6-methylcyclohexane carboxylate, e.g., "ERL-4201" (obtained from Union Carbide Corp.), bis(3,4-epoxy-6-methylcyclohexylmethyl) adipate, e.g., "ERL-4289" (obtained from Union Carbide Corp.), 2-(3,4-epoxycyclohexyl-5,5-spiro-3,4-epoxy)cyclohexenemetad ioxane, e.g. "ERL-4234" (obtained from Union Carbide Corp.), and epoxidized polybutadiene, e.g. "Oxiron 2001" (obtained from FMC Corp.)

Reactive diluents containing one epoxide group such as t-butylphenyl glycidyl ether, may also be used. The reactive diluent may comprise up to 25 percent by weight of the epoxide component.

The epoxy resins of the present invention can be employed for most applications in which present commercial epoxy resins are employed including surface coatings. By reason of their flexibility, impact strength, high glass transition temperatures (Tg), and low moisture pick up properties, the epoxy resins of the present invention are particularly well suited for use as the resin binder in the manufacture of composites to be employed in high temperature environments. Such composites are prepared by (1) impregnating webs or tapes with fibers such as glass, graphite, quartz, silicon carbide, alumina, titania, poly(benzothiazole), poly(benzimidazole), poly(benzoxazole), aromatic polyamides, and other organic fibers, and the curable composition of epoxy resin and hardner and (2) curing layups of the impregnated webs or tapes at elevated temperatures under pressure and frequently under reduced pressure.

Certain of the cured epoxy resins of the present invention have quite low dielectric constants. The resins of formula (II) are preferred resins having such properties. Composites manufactured with these resins are well suited for use as circuit boards in the electronic industry.

The epoxy resins of the present invention are excellent adhesives, particularly for bonding metals to metals, composites to composites, and metals to composites. Thin webs of high melting fibers, as described supra, which are impregnated with a curable composition of an epoxy resin and a hardener and partially cured, can be interposed between structures to be bonded. Such assemblies then can be cured under pressure to prepare assemblies which are otherwise difficult to prepare.

The present invention is more fully illustrated by the following non-limiting examples:

EXAMPLE 1

This example illustrates the preparation of the epoxy identified supra as BPAE and having the structure as shown in formula (III).

2 L, 3 necked flask equipped with a mechanical stirrer, addition funnel, a reflux condenser, a thermometer, and a water bath, was charged with 390 grams (4.21 moles, 330 ml) of epichlorohydrin, 97.5 grams (2.03 moles, 125 ml) of 100% ethyl alcohol, 13 ml (13 grams, 0.70 mole) of $H_2O$, and 102.63 grams (0.25 mole) of the diamine prepared by reacting bisphenol A with 1-chloro-4-nitrobenzene and subsequently reducing the nitro groups to amino groups. The mixture was then heated and kept at 80° C. for 4.5 hours. A brown solution formed. After this period, the reaction was cooled and held at 60° C. At this point, 100 grams of 50% NaOH solution (by weight) (1.25 mole, 50 grams of NaOH, and 50 ml of water) was added to the mixture over a 3.5 hour period. An extra 50 ml of water was added from rinsing the addition funnel and then the flask contents were held an additional 30 minutes at 60° C. At this stage, white NaCl salt had formed at the walls of the flask. Afterward, the excess epichlorohydrin was removed under a vacuum (water aspirator of 27" of $H_2O$) at 65° C. Then, 2.20 L of toluene (1905 grams, 21 mole) was added in 400 ml portions. This was done by first adding the toluene, washing the solution with 400 ml of water, discarding the water layer, adding the next portion of toluene, and washing the solution with 400 ml of $H_2O$ again. By this action, the NaCl formed during the reaction was separated from the product. The toluene solution was then removed under a vacuum at 29" of $H_2O$ and pot temperature of 140° C. (ROTOVAC was used). After most of the solvent was removed, the vacuum distillation was stopped and instead, a pump was used as a better vacuum in the removal of the rest of the solvent in conjugation with the ROTOVAC. The product was a brown viscous liquid which hardened upon cooling at room temperature.

The yield was 154.21 grams of epoxy which is 97% of the theoretical yield.

The epoxy equivalent weight was 186 (theory 159) and was determined by following "Determination of Epoxy Content in MY-720," Cibai-Geigy Test Method No. 200, Ciba-Geigy Company Resin Department (1977).

EXAMPLE 2

This example illustrates the preparation of the epoxy having the structure as in formula (II).

A two liter three necked flask equipped with a mechanical stirrer, addition funnel, a reflux condenser, thermometer, and water bath was charged with 220 ml (2.813 moles) epichlorohydrin, 600 ml (10.28 moles) of 100% ethanol, 20 ml (1.11 moles) water, and 70 grams (0.135 moles) hexafluorobisphenol A modified diamine. The diamine dissolved. The mixture was then heated and kept at 80° C. for longer than 4.5 hours. A brown solution was formed. After this, the reaction was cooled and held at 60° C. At this point, 30 grams (0.75 moles) of NaOH [as a 50% solution] was added to the mixture over a 3 hour period by using an addition funnel. An extra 50 ml water was added from rinsing the addition funnel. The flask contents were then held an additional 30 minutes at 60° C. At this stage, white NaCl salt had formed at the walls of the flask. Afterwards, the excess epichlorohydrin was removed under a vacuum (water aspirator of 27 inches water) at 65° C. then 400 ml toluene was added The product was washed three times with water and extracted. The resulting solution was filtered through activated charcoal and was dried with $MgSO_4$. The resulting solution was vacuum distilled at 100° C. and was weighed. The yield was 64.2 grams of epoxy resin which is 67% of the theoretical yield.

EXAMPLE 3

This example illustrates the preparation of an epoxy prepared from bis[4-(4-aminophenoxy)phenyl]sulfone.

A two liter three necked flask equipped with a mechanical stirrer, addition funnel, reflux condenser, thermometer, and water bath were charged with 780 grams (660 ml, 8.43 moles) epichlorohydrin, 300 ml (5.076 moles) of 100% ethanol, 36 grams (36 ml, 2 moles) water, and 216.5 grams (6.5 moles) sulfone diamine of the present invention. The diamine dissolved. The mixture was then heated and kept at 80° C. for 4.5 hours. A brown solution was formed. After this period, the reaction was cooled and held at 60° C. At this point, 100 grams of 50% NaOH (1.25 moles, 50 grams of NaOH and 50 ml of water) was added to the mixture over a 3.5 hour period by using the addition funnel. An extra 50 ml water was added by rinsing the addition funnel. The flask contents were then held an additional 30 minutes at 60° C. At this stage, white NaCl salt had formed at the walls of the flask. Afterwards, the excess epichlorohydrin was removed under vacuum (water aspirator of 27 inches $H_2O$) at 65° C. Then, 2598 grams (three liters, 28.6 moles) toluene were added in 400 ml portions. This was done by first adding the toluene, then washing the solution with 400 ml of water, discarding the water layer, adding the next portion of toluene, and washing the solution with 400 ml water again. By this action, the NaCl formed during the reaction was separated from the product. Then, the toluene solution was removed under vacuum of 29 inches water at a pot temperature of 140° C. A ROTOVAC was used. After most of the solvent was removed, the vacuum distillation was stopped and instead, a pump was used for better vacuum in the removal of the rest of the solvent in conjugation with the ROTOVAC. The product was a brown viscous liquid which hardened upon cooling at room temperature. The yield was 215 grams of epoxy resin which is 66% of the theoretical yield. The epoxy equivalent weight was 198 (theory 164) and was determined according to the method cited in Example 1.

EXAMPLE 4

The epoxy resins of Examples 1 and 3 were each combined with DDS in a ratio of 1.00 mole of epoxy resin to 0.87 mole of DDS and cured to prepare specimens for determination of Tg. As a control, 1.0 equivalent of a commercial sample of TGMDA was blended with 0.87 of DDS and cured. The first cure and post-cure cycle was the one recommended by the TGMDA supplier for the TGMDA/DDS formulation. This cycle was 2 hrs. at 80° C., 1 hr. at 100° C., 4 hours at 150° C., and 7 hours at 250° C. The castings were machined into test specimens for dynamic mechanical analysis (2° C./min., $N_2$ atmosphere). The glass transition temperature of each formulation was measured by determining the peak maximum of the log (flexural loss modulus) curve.

EXAMPLE 5

Table I sets forth comparative data for Ciba-Geigy's TGMDA, Shell's EPON HPT 1072, and the resin of Example 1. The TGMDA and EPON HPT 1072 data were obtained from literature; Tg wet for EPON HPT 1072 was not published. It should be noted that the TGMDA and the EPON HPT 1072 both contained toughening components such as a phenolic epoxy while the BPAE did not contain a toughening component.

TABLE I

|  | TGMDA/DDS | EPON HPT 1072/DDS | EX 1 RESIN/DDS | EX 1 RESIN/BPADA |
|---|---|---|---|---|
| Parts by Weight | 100/44 | 100/36.6 | 100/29 | 100/47 |
| Tg dry | 242 | 242 | 238 | 218 |
| wet | 168 | — | 219 | 205 |
| R.T. Flexure |  |  |  |  |
| Modulus, ksi | 575 | 539 | 554 | 505 |
| Ult. Strength, ksi | 17.0 | 10.1 | 14.7 | 13.4 (minimum) |
| Elongation, % | 3.6 | 2.1 | 3.8 | 4.0 (minimum) |
| Moisture Gain, % | 4.8 | 2.52 | 2.41 | 1.68 |
| Tg Moisture Sensitivity, °C./% | 15 | — | 8 | 8 |
| Uncured formulation Tg | 18 | 41 | 26 | 51 |

For the EX 1 resin, the moisture gain was determined by weighing the dry sample, immersing the sample in boiling water for about 72–108 hours, and weighing the wet sample to determine the weight change due to moisture gain. As Table I indicates, the moisture gain of the epoxy resins of the present invention is less than that of known epoxy resins. The moisture gain for the resin of Example 1 is only half that of TGMDA and the resulting reduction in Tg is not nearly as severe. The flexural properties of the resin of Example 1 are similar to that of TGMDA.

EXAMPLE 6

Table II sets forth thermogravimetric analysis (hereinafter TGA) results for TGMDA and the resin of Example 1.

TABLE II

|  | TGMDA/DDS | EX 1 RESIN/DDS | TGMDA/BPADA | EX 1 RESIN/BPADA |
|---|---|---|---|---|
| % Wt. Loss at 400° C. | 42 | 30 | 28 | 11 |

This shows that the resins of the present invention have better thermal stability then comparable conventional resins.

EXAMPLE 7

A single graphite composite panel was molded by using the resin of Example 1 with DDS in a ratio of 1.00 mole of epoxy resin to 0.87 mole of DDS. The mechanical property data are set forth in Table III.

TABLE III

| Short Beam Shear Strength, ksi | 7.54 |
|---|---|
| R.T. Flexure |  |
| Modulus, msi | 9.13 |
| Ult. Strength, ksi | 101.0 |
| R.T. Tensile |  |
| Modulus, msi | 7.83 |
| Ult. Strength, ksi | 82.8 |
| Elongation, % | 1.03 |

Certain description of the epoxy resins of the present invention and their properties are described in the paper of M. M. Emad, R. P. Chartoff, J. A. Harvey, "The Use of Thermal Analysis to Evaluate the Curing of a New Family of Aromatic Ether Epoxy Resins," *Proceedings of the Fifteenth North American Thermal Analysis Society Conference*, 430 (1986) which is incorporated herein by reference.

Having described the invention in detail and by reference to preferred embodiments thereof, it will be apparent that modifications and variations are possible without departing from the scope of the invention defined in the appended claims.

What is claimed is:

1. An epoxy resin of the formula

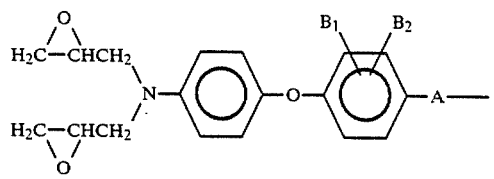

-continued

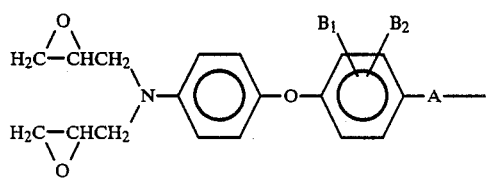

wherein A is —C(CH$_3$)$_2$— and B$_1$, B$_2$, B$_3$, and B$_4$ are —H.

2. An epoxy resin of the formula

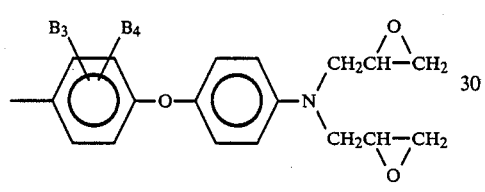

wherein A is —C(CF$_3$)$_2$— and B$_1$, B$_2$, B$_3$ and B$_4$ are —H.

3. A curable composition comprising an epoxy resin of the formula

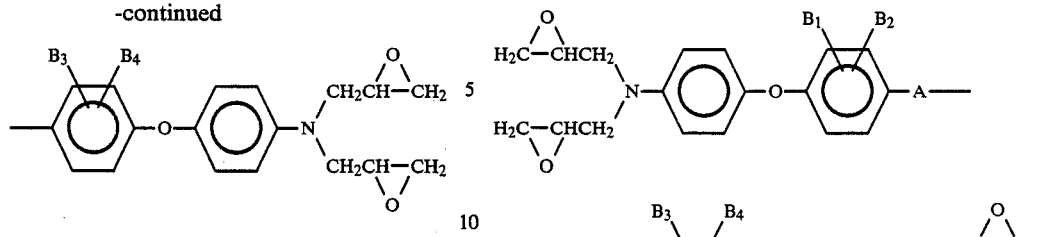

wherein A is —C(CH$_3$)$_2$— and B$_1$, B$_2$, B$_3$, and B$_4$ and —H, and an effective curing amount of a hardener for epoxy resin.

4. A curable composition comprising an epoxy resin of the formula wherein A is —C(CF$_3$)$_2$— and B$_1$, B$_2$, B$_3$ and B$_4$ are —H, and an effective amount of a hardener for epoxy resin.

* * * * *